United States Patent [19]
Gaenzler et al.

[11] 3,952,045
[45] Apr. 20, 1976

[54] METHOD FOR PREPARING CARBONIC ACID ESTERS

[75] Inventors: Wolfgang Gaenzler, Darmstadt-Arheilgen; Guenter Schroeder, Ober-Ramstadt; Klaus Kabs, Seeheim, all of Germany

[73] Assignee: Röhm GmbH, Darmstadt, Germany

[22] Filed: July 3, 1974

[21] Appl. No.: 485,630

[30] Foreign Application Priority Data
July 9, 1973    Germany............................ 2334736

[52] U.S. Cl. ............................................... 260/463
[51] Int. Cl.² ........................................ C07C 68/00
[58] Field of Search ................................. 260/463

[56] References Cited
UNITED STATES PATENTS

| | | |
|---|---|---|
| 3,114,762 | 12/1963 | Mador et al. ....................... 260/463 |
| 3,227,740 | 1/1966 | Fenton............................... 260/463 |
| 3,227,741 | 1/1966 | Fenton............................... 260/463 |
| 3,445,497 | 5/1969 | Anderson et al. .............. 260/463 X |
| 3,625,995 | 12/1971 | Brattesani....................... 260/463 X |
| 3,846,468 | 11/1974 | Perrotti et al....................... 260/463 |

*Primary Examiner*—Joseph P. Brust
*Attorney, Agent, or Firm*—Curtis, Morris & Safford

[57] ABSTRACT

A method for preparing carbonic acid esters,

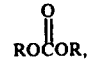

by reacting an alcohol, ROH, with carbon monoxide and oxygen in the presence of a catalyst comprising a copper salt, chloride or bromide, and an organic phosphorus compound such as a phosphine oxide, phosphite, phosphate, or phosphonate.

3 Claims, No Drawings

METHOD FOR PREPARING CARBONIC ACID ESTERS

The present invention relates to a method for preparing carbonic acid esters. More in particular, the invention relates to a method for preparing carbonic acid esters by the reaction of an alcohol with carbon monoxide and oxygen in the presence of a catalytic system comprising copper, chloride or bromide, and certain organic phosphorus compounds.

Ever since polycarbonates have assumed a significant role as valuable synthetic resins, carbonic acid esters have achieved a corresponding significance. It is known that polycarbonates can be produced by the reactionn of glycols or diphenols with alkyl-, alkylaryl-, or aryl-carbonates. In the production of polycarbonates on a commercial scale, the reaction of bisphenol A with phosgene or the esterification of this diphenol with carbonic acid esters has played a particularly important role. Heretofore, the last-mentioned esters have been obtained by reaction of an alcohol with phosgene or chloroformic acid ester in the presence of an inorganic or organic basic compound. According to German Offenlegungsschrift No. 2, 110, 194, carbonic acid esters are obtained by the reaction of an alcohol with carbon monoxide and oxygen in the presence of a catalyst comprising a compound of a complex-forming metal of Group IB, IIB, or VIII of the Periodic System. Supported by examples, the teaching of the German specification that the reaction gives a quantitative yield calculated on the reactants employed appears to leave no doubt of the practical utility of the method. The prior art examples teach yields of dimethylcarbonate of 96.2 percent; of diethylcarbonate, 97.5 percent; and of dibenzylcarbonate, 96 percent, in each case calculated on the copper present in the catalyst. However, if one uses the same calculation to compute the yield of the process according to the present invention, that is if one bases the amount of carbonic acid ester obtained on the amount of copper contained in the catalyst, one obtains a value, for example in following Example 3, of about 4350 percent!

It is evident that a process which would, according to Example 1 of DOS No. 2,110,194, utilize 424 tons of copper chloride for the production of 370 tons of dimethylcarbonate could not be called a process of interest for large scale operations. (A fourth example in the aforementioned German publication involves a continuous performance of the prior art process over a period of about 5 hours. No data are reported which permit a statement concerning the efficacy of copper chloride — the only catalytic metal compound exemplified in this German application — in a continuous performance of the process.)

It has now been found that carbonic acid esters of the formula

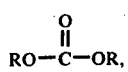

in which R is an alkyl, aralkyl, or cycloalkyl group (i.e. a hydrocarbon group), can be prepared by the reaction of an alcohol, ROH, where R has its earlier meaning, with carbon monoxide and oxygen in the presence of a catalyst in part containing copper. In the process of the present invention, the reaction takes place in the presence of a catalyst system, initially present or formed during the reaction, comprising a copper salt. If this salt is not a chloride or bromide, the catalyst system also contains a chloride or bromide, soluble in the reaction medium, of a metal other than copper. Further, the catalyst system contains a phosphine oxide or an organic phosphite, phosphate, or phosphonate. It should be mentioned that the efficacy of catalytic systems in which chloride is present is greater than that of systems containing bromide. Nevertheless, even the bromine-containing catalysts give a significant improvement in comparison with the process of DOS No. 2,110,194.

The catalytic efficacy of the systems to be employed according to the present invention can be improved if the systems additionally contain a compound of a transition metal of the third to seventh sub-groups of the Periodic System, although at present no satisfactory explanation can be given for this effect. Compounds of cerium, titanium, tantalum, tungsten, and rhenium can be used to particular advantage. In addition to an evident improvement of the catalytic efficacy of such combinations, which are hypothesized to be binuclear complexes, the use of soluble salts of the aforementioned transition metals increases the solubility of copper-I-chloride of copper-I-bromide in methanol or other of the alcohols used as the reaction medium. Exemplary of suitable catalyst components of this type are cerium-III-chloride, titanium tetrachloride, titanium dichloride-dimethylate, zirconium tetrachloride, vanadium oxychloride, tantalum dichloride-trimethylate, trichloro-trimethanolo-chromium-III, tungsten oxytetrachloride, and rhenium pentachloride.

As alcohols suitable for employment in the process of the invention, methanol, ethanol, isopropanol, butanol, benzyl alcohol, and cyclohexanol can be mentioned as exemplary.

The organic phosphorus compounds which can be used in the invention include the triaryl phosphine oxides, for example triphenyl phosphine oxide, and also alkyl- or halo-substituted triaryl phosphine oxides such as tris-p-chlorophenyl phosphine oxide or tris-p-toluyl phosphine oxide.

They also include phosphites. Particularly suitable phosphites are the lower alkyl, lower alkylene, and phenyl phosphites, such as triethyl phosphite or triallyl phosphite.

Phosphates may also be employed according to the invention. Lower alkyl and lower haloalkyl phosphates such as triethyl phosphate, tris-(2-chloroethyl)-phosphate, tris-(2-bromoethyl)-phosphate, and tris-(2,3-dibrompropyl) phosphate are particularly suitable, as are oligophosphates such as the oligophosphate shown in following Example 11, which material is available under the tradename "Phosgard C-22-R".

Also, phosphonates, for example,

can be employed according to the present invention, as is shown in greater detail in the Examples.

By the introduction of phosphorus trichloride or phosphorus pentachloride, for example, into alcohol, it is known that the corresponding esters of phosphorous acid or phosphoric acid are formed. Accordingly, the phosphites or phosphates which are employed according to the invention can be formed in situ in the reaction mixture by reaction of the alcohol employed with the corresponding phosphorus halides.

Although copper is used in the form of its chloride or bromide with particular advantage in the preparation of the novel catalytic systems of the invention, one can also employ other copper salts soluble in the reaction medium, such as the acetate, sulfate, nitrate, cyanate, or acetylacetonate. However, in such a case the presence of a soluble chloride or bromide of a different metal is necessary.

Concerning the nature of the catalytically effective systems, it can be said with some certainty that they involve complex copper compounds in whose structure phosphorus or phosphorus-containing groups and chlorine or bromine are present as ligands. In these complexes, copper-I is present as a central atom having at least two and at most four ligands joined thereto, of which at least one ligand must be halogen and at least one must be a phosphorus compound. In complexes of copper-II, again at least one halogen ligand and at least one phosphorus-containing ligand must be present, but the maximum number of ligands can be six (of which one to five may be halogen and the balance phosphorus-containing, or vice versa). The investigation of numerous complexes of this type has led to the surprising discovery that such complexes in which univalent copper is present as the central atom are particularly effective catalysts when the molar ratio copper-I:chlorine or bromine: phosphorus is about 1:1:1. However, if complexes in which copper-II is the central atom are employed, the molar ratio copper-II:chlorine or bromine:phosphorus should be about 1:2:2.

The co-use of compounds of metals of the third to seventh sub-groups of the Periodic System is the preparation of catalysts has already been mentioned. Systems of this type are shown in following Examples 1, 3, 4, 7, 8, 12, 15, 16, and 27 – 29. When these compounds are present they are suitably employed in an amount such that the molar ratio transition metal:copper in the catalyst systems is between about 1:1 and 10:1.

The amount of catalyst employed in practicing the method of the invention can vary over wide limits. For example, the ratio of the weight of catalyst to the weight of alcohol reacted can be between about 1:10 and 1:10,000.

The components of the catalyst can be combined to preform a catalyst complex prior to use, which complex is then dissolved in a catalytic amount in the reaction medium, or can be added per se to the reaction medium to form the catalyst system in situ.

The process according to the present invention requires the use of pressure. More in particular, the partial pressure of carbon monoxide and oxygen, in combination, can vary between certain limits, for example 10 atmospheres to 150 atmospheres. If oxygen is employed in the form of air, it is suitable to employ a higher pressure than when the oxidation proceeds in the presence of pure oxygen.

The reaction temperature also can vary between certain limits, for example between 100°C. and 250°C.

A better understanding of the invention and of the many advantages thereof can be had from the following specific examples, given by way of illustration. In the examples, the following procedure was employed except where otherwise noted.

The reaction medium, comprising the catalyst system and an alcohol as a solvent, is introduced into a "Teflon"-coated heatable 2-liter autoclave. The autoclave is then closed. 40 atmospheres of carbon monoxide and 20 atmospheres of oxygen are introduced at room temperature and the autoclave is then heated to 140°C. – 150°C. The pressure falls very sharply during the course of the reaction. After cooling, the autoclave is opened and the contents are processed by distillation. The carbonate obtained is identified with the aid of nuclear magnetic resonance spectroscopy, mass spectroscopy, and gas chromatography.

EXAMPLE 1

2 g of cerium-IV-sulfate, 2 g of copper-II-chloride, and 3 g of triphenyl phosphine oxide are refluxed in 700 ml of methanol for 2 hours. The reaction solution is then introduced into an autoclave and combined as described above with carbon monoxide and oxygen. 90.6 g of dimethylcarbonate are formed.

EXAMPLES 2 – 15

The following examples, summarized in Table I below, are carried out as in Example 1 using a partial pressure of carbon monoxide of 40 atmospheres, a partial pressure of oxygen of 20 atmospheres, and 700 ml of methanol as the solvent.

TABLE I

| Example No. | Catalyst Components (in g) | Dimethylcarbonate (in g) |
|---|---|---|
| 2 | 2 $Cu_2Cl_2$; 2 $CuCl_2$ <br> 3,8 tris(2,3-dibrompropyl)-phosphate | 67.8 |
| 3 | 2 $TiCl_2(OCH_3)_2$; 2 $CuCl_2$, <br> 2 $O=P(C_6H_5)_3$ | 78.5 |
| 4 | 2 $TaCl_2(OCH_3)_3$; 2 $Cu_2Cl_2$; 2 $CuCl_2$ <br> 2 $O=P(C_6H_5)_3$ | 76.5 |
| 5 | 2 $Cu_2Cl_2$; 2 $CuCl_2$; 2 $O=P(C_6H_5)_3$ | 69.8 |
| 6 | 4 $Cu_2Cl_2 \cdot PCl_3$ | 69.3 |
| 7 | 2 $CuCl_2$; 2 $WOCl_4$; 2 $O=P(C_6H_5)_3$ | 61.4 |
| 8 | 2 $ReCl_5$; 2 $Cu_2Cl_2$; 2 $CuCl_2$, <br> 2 $O=P(C_6H_5)_3$ | 58.9 |
| 9 | 2 $Cu_2Cl_2$; 5 KCl <br> 2 $O=P(C_6H_5)_3$ | 51.1 |
| 10 | 2 $CuCl_2$; 2 triallylphosphite | 48.4 |
| 11 | 2 $Cu_2Cl_2$; 2 $CuCl_2$ <br> 4 g of an oligophosphate of the formula | 47.7 |

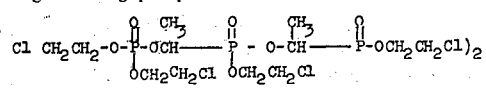

TABLE I-continued

| Example No. | Catalyst Components (in g) | Dimethylcarbonate (in g) |
|---|---|---|
| 12 | 2 $Cu_2Cl_2$; 2 grams of a phosphonate of the formula $CH_3CH_2\overset{O}{\underset{\|}{P}}(OC_2H_5)_2$ | 44.4 |
| 13 | 2 $Cu_2Cl_2$; 2 triethylphosphite | 42.8 |
| 14 | 2 $Ce(SO_4)$, 2 $CuBr_2$, 2 $\overset{O}{\underset{\|}{P}}(C_6H_5)_3$ | 13.6 |

EXAMPLE 15

2 g of tantalum dichlorotrimethylate, 2 g of copper-II-chloride, and 5 g of triphenyl phosphine oxide are dissolved in 700 ml of benzyl alcohol. Carbon monoxide and oxygen are introduced as described above. An infrared spectroscopic examination of the reaction product confirms the expected formation of dibenzylcarbonate.

EXAMPLES 16 – 24

As described earlier, the oxygen required by the method can also be employed in the form of air. In the following examples, as already described earlier herein, an alcohol (methanol) is reacted with carbon monoxide and air in the presence of the copper complex indicated. As in the aforementioned examples, in each case 700 ml of methanol are present in which 2 g of the catalyst are dissolved. The formation of dimethylcarbonate follows after 40 atmospheres of carbon monoxide and 40 atmospheres of air are introduced. The initial reaction temperature is 140°C. – 150°C. The carbonate formed is identified as already disclosed earlier herein. The results are set forth in following Table II. In Examples 16 and 19 – 23, the copper is present as copper-I. In Examples 17, 18, and 24, the copper is present as copper-II.

TABLE II

| Example No. | Catalyst System | Dimethylcarbonate (in g) |
|---|---|---|
| 16 | $CuBr.P(OCH_3)_3$ | 12.9 |
| 17 | $CuCl_2[O=P(C_6H_5)_3]_2$ | 8.7 |
| 18 | $CuBr_2[O=P(C_6H_5)_3]_2$ | 8.5 |
| 19 | $CuCl\ P(OC_6H_5)_3$ | 15.6 |
| 20 | $CuCl[P(OC_6H_5)_3]_2$ | 3.5 |
| 21 | $CuBr\ P(OC_6H_5)_3$ | 10.5 |
| 22 | $CuBr[P(OC_6H_5)_3]_2$ | 2.2 |
| 23 | $CuBr.P(OCH_3)_3$ | 12.9 |
| 24 | $CuCl_2[P(OC_6H_5)_3]_2$ | 19.7 |

EXAMPLES 25 – 28

The procedure of Examples 16 – 24 is repeated except that 20 atmospheres of oxygen are introduced instead of 40 atmospheres of air. All other reaction conditions remain the same as in Example 16 – 24.

The components of the catalyst system (in grams) and the yield of product produced in the Examples is given below in Table III:

TABLE III

| Example No. | Catalyst System | Dimethylcarbonate (in g) |
|---|---|---|
| 25 | 2.5 $Cu(NO_3)_2$<br>5 KCl<br>2[$O=P(C_6H_5)_3$] | 13.8 |
| 26 | 2 $CuCl_2$<br>2 $MoCl_5$ | 47.2 |
| 27 | 10[$O=P(C_6H_5)_3$]<br>2 $CuCl_2$<br>2 $LaCl_3$<br>2[$O=P(C_6H_5)_3$] | 45.4 |
| 28 | 2 $CuBr_2$<br>2.5 $NbCl_2(OCH_3)_3$<br>2[$O=P(C_6H_5)_3$] | 18 |

EXAMPLE 29

2 g of copper-I-bromide are dissolved with 4 g of triphenyl phosphine oxide in 700 ml of n-butanol. 60 atmospheres of carbon monoxide and 40 atmospheres of compressed air are then introduced under pressure. 18 g of butylcarbonate are obtained.

EXAMPLE 30

2 g of copper-II-bromide, 2 g of dihydro-hexaaceto-trichromium-III-diacetate, and 5 g of triphenyl phosphine oxide are dissolved in 600 ml of ethanol. 25 atmospheres of compressed air and 40 atmospheres of carbon monoxide are then introduced under pressure. 15 g of diethylcarbonate are obtained.

What is claimed is:

1. In the method of making a carbonic acid ester of the formula $$ROCOR$$
$$\|$$
$$O\ ,$$

$$ROCOR$$
$$\|$$
$$O\ ,$$

wherein R is alkyl, aralkyl, or cycloalkyl, by reacting an alcohol, ROH, wherein R has its earlier meaning, with carbon monoxide and oxygen in the presence of a catalyst system consisting essentially of copper, a halide, and an organic phosphorus compound, the improvement wherein the reaction is carried out at a temperature from 100° to 250°C. under a combined pressure of oxygen and carbon monoxide between 10 and 150 atmospheres in the presence of a catalyst system, soluble in the ROH reaction medium, consisting essentially of cuprous or cupric copper, chloride or bromide, and an organic phosphorus compound selected from the group consisting essentially of triphenyl phosphine oxide; halo- and alkyl-substituted triphenyl phosphine oxides; lower alkyl-, lower alkylene-, and phenyl-phosphites; lower alkyl- and lower haloalkyl-phosphates and oligophosphates thereof; and ethyl phosphonic acid diethyl ester, the ratio Cu:halide:phosphorus compound in said catalyst system being about 1:1:1 for cuprous copper and about 1:2:2 for cupric copper.

2. The method as in claim 1 wherein a compound of a transition metal of the third to seventh sub-groups of the Periodic System is additionally present in said catalyst system.

3. The method as in claim 2 wherein said transition metal compound is a chloride or a bromide.

* * * * *